United States Patent [19]

Weber et al.

[11] 4,100,027
[45] Jul. 11, 1978

[54] PROCESS FOR THE PREPARATION OF 4-ANDROSTENE-3,17-DIONE DERIVATIVES

[75] Inventors: Alfred Weber; Mario Kennecke; Rudolf Mueller; Ulrich Eder; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 751,687

[22] Filed: Dec. 16, 1976

[30] Foreign Application Priority Data

Dec. 19, 1975 [DE] Fed. Rep. of Germany ....... 2558088

[51] Int. Cl.² ............................................. C07B 29/00
[52] U.S. Cl. ................................................. 195/51 G
[58] Field of Search ...................................... 195/51 G

[56] References Cited

U.S. PATENT DOCUMENTS

| 3,388,042 | 6/1968 | Arima et al ...................... | 195/51 G |
| 3,684,656 | 8/1972 | Waard ............................... | 195/51 G |
| 3,759,791 | 9/1973 | Marsheck et al ................. | 195/51 G |

Primary Examiner—Alvin E. Tanenholtz
Attorney, Agent, or Firm—Millen & White

[57] ABSTRACT

A process for the preparation of 4-androstene-3,17-dione derivatives of the formula

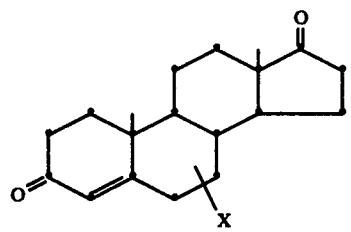

wherein X is 6,7-methylene or fluoro, chloro, or methyl in the 6- or 7-position, comprises fermenting a sterol of the formula

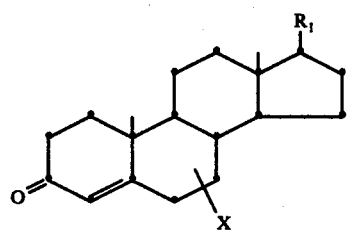

wherein X is as above and $R_1$ is a hydrocarbon residue of 8-10 carbon atoms with a microorganism culture capable of degrading the side chain of a sterol.

10 Claims, No Drawings

PROCESS FOR THE PREPARATION OF 4-ANDROSTENE-3,17-DIONE DERIVATIVES

BACKGROUND OF THE INVENTION

Numerous microorganisms, for example, those of the genera Arthrobacter, Brevibacterium, Microbacterium, Protaminobacter, Bacillus, Norcardia, Streptomyces, and especially Mycobacterium, are capable of degrading zoosterols and phytosterols to carbon dioxide and water. During the degradation, 4-androstene-3,17-dione and 1,4-androstadiene-3,17-dione are formed as intermediates.

The degradation of the sterols to avoid further degradation of the thus-formed 4-androstene-3,17-dione or 1,4-androstadiene-3,17-dione is accomplished by using inhibiting additives or mutated microorganisms. See DOS's (German Unexamined Laid-Open Applications) 1,543,269 and 1,593,327, and U.S. Pat. No. 3,684,657.

SUMMARY OF THE INVENTION

This invention relates to a process for the preparation of a 4-androstene-3,17-dione compound of Formula I

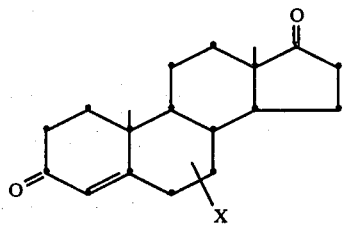

wherein X is 6,7-methylene or 6- or 7-fluoro, chloro, or methyl, comprising fermenting a sterol of Formula II

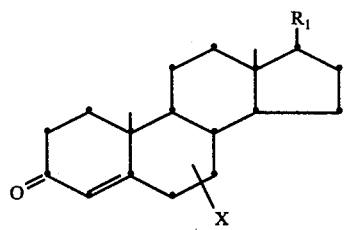

wherein X is as above and $R_1$ is a saturated or unsaturated hydrocarbon sterol side chain of 8–10 carbon atoms, with a microorganism culture capable of degrading sterol side chains.

DETAILED DESCRIPTION

Hydrocarbon residue $R_1$ of 8–10 carbon atoms is a hydrogenated or unsaturated side chain of a naturally occurring zoosterol or phytosterol, for example, of cholesterol, stigmasterol, campesterol, brassicasterol, or the sitosterols.

Sterol compounds of Formula II include compounds of Formula IIa

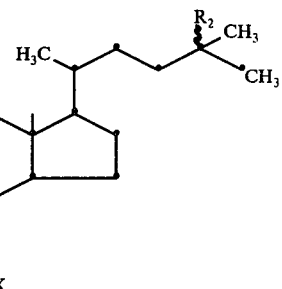

wherein X is as above and $R_2$ is hydrogen, methyl or ethyl.

Typical starting compounds for the process of this invention are, for example, sterols of Formula IIa wherein X is 6α-fluorine, 6α-methyl, 6α,7α- or 6β,7β-methylene, 7α-methyl, or 7β-methyl. Examples of typical starting compounds are:
6α-fluoro-4-cholesten-3-one,
6α-methyl-4-cholesten-3-one,
7α-methyl-4-cholesten-3-one,
7β-methyl-4-cholesten-3-one,
6α-fluoro-4-stigmasten-3-one,
6α-methyl-4-stigmasten-3-one,
7α-methyl-4-stigmasten-3-one,
7β-methyl-4-stigmasten-3-one, 6α-fluoro-4-campesten-3-one,
6α-methyl-4-campesten-3-one, 7α-methyl-4-campesten-3-one,
7β-methyl-4-campesten-3-one,
and
corresponding sitosterol compounds.

The process of this invention is done under the same fermentation conditions which are used for conventional microbiological side chain degradation reactions of sterols, except for the use of different starting compounds and absence of inhibitors.

The fermentation is conducted using microorganism cultures customarily employed for side chain degradation of sterols. Suitable cultures include, for example, bacterial cultures of the genera Arthrobacter, Brevibacterium, Microbacterium, Protaminobacter and Streptomyces.

Examples of suitable microorganisms include: *Microbacterium lactum* IAM-1640, *Protaminobacter alboflavus* IAM-1040, *Bacillus roseus* IAM-1257, *Bacillus sphaericus* ATCC-7055, *Norcardia gardneri* IAM-105, *Norcardia minima* IAM-374, *Norcardia corallina* IFO-3338, *Streptomyces rubescens* IAM-74, *Mycobacterium avium* IFO-3082, *Mycobacterium phlei* IFO-3158, *Mycobacterium phlei* (Institute of Health, Budapest No. 29), *Mycobacterium phlei* ATCC-354, *Mycobacterium smegmatis* IFO-3084, *Mycobacterium smegmatis* ATCC-20, *Mycobacterium smegmatis* (Institute of Health, Budapest No. 27), *Mycobacterium smegmatis* ATCC-19979, *Mycobacterium fortuitum* CBS-49566, *Mycobacterium spec.* NRRL-B-3805, and *Mycobacterium spec.* NRRL-B-3683.

Mycobacteria are the preferred organisms, most preferably *Mycobacterium spec.* NRRL-B-3805, and *Mycobacterium phlei* ATCC-354.

Submerged cultures are grown with aeration in a suitable nutrient medium. Then, the substrate, dissolved in a suitable solvent or preferably in an emulsion, is added to the cultures and the fermentation is conducted until maximum substrate conversion has been attained.

Typical solvents for the substrate are, for example, methanol, ethanol, glycol monomethyl ether, dimethylformamide, and dimethyl sulfoxide. The substrate can be emulsified, for example, by adding substrate in micronized form or dissolved in a water-miscible solvent, such as methanol, ethanol, acetone, glycol monomethyl ether, dimethylformamide, or dimethyl sulfoxide, with a nozzle under turbulent mixing conditions to preferably decalcified water containing customary emulsifying agents. Suitable emulsifying agents are nonionic emulsifiers, for example, ethylene oxide adducts or fatty acid esters of polyglycols, e.g., commercially available surfactants such as "Tegin", "Tween", and "Span".

The fermentation is conducted under conventional conditions (G. S. Fonken and R. A. Johnson: Chemical Oxydations with Microorganism: Macel Dekker Inc., New York 1972.

The optimum substrate concentration, time of substrate addition, and duration of fermentation depend on the structure of the substrate and on the type of the microorganism. These variables are determined, as is generally necessary in microbiological steroid conversions, in each individual case by preliminary tests, which are well-known to those skilled in the art.

A surprising aspect of this invention is that, under otherwise conventional conditions, the side chains of sterol derivatives of Formula II are degraded selectively, because it is known that side chain degradation of sterols is caused by very complex fermentation systems, and it is unexpected that the enzymes causing side chain degradation of natural steroids would be able to effect side chain degradation of sterol compounds of Formula II, which do not occur naturally. Moreover, it could not be foreseen that enzyme systems which degrade 1,4-androstadiene-3,17-dione and 4-androstene-3,17-dione are incapable of further degrading compounds of Formula I.

4-Androstene-3,17-dione compounds of Formula I obtainable in accordance with this invention are valuable intermediates for the snythesis of pharmacologically active steroids, e.g., 6,7$\beta$-methylene-spirolactone, 17$\beta$-hydroxy-7$\alpha$,17$\alpha$-dimethyl-4-androsten-3-one, 6-chloro-11,17$\alpha$,21-trihydroxy-1,4,6-pragnatriene-3,20-dione and 17$\alpha$-acetoxy-6-chloro-4,6-pregnadiene-3,20-dione.

It is possible, for example, to reduce the 17-keto group of a 4-androstene-3,17-dione compound, optionally after ketalization of the 3-oxo group; or to react the 17-keto group with an organometallic compound of Formula IV MeR$_4$     IV wherein R$_4$ is alkyl, alkenyl, or alkynyl of up to 4 carbon atoms and Me is an alkali metal atom or a magnesium halide residue to obtain, after removing the ketal group which may be present, a 17$\beta$-hydroxy-4-androsten-3-one of Formula III

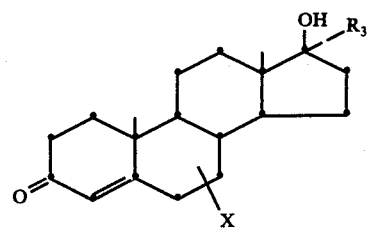

wherein X is as above and R$_3$ is R$_4$ or hydrogen.

R$_3$ and R$_4$ are alkyl, alkenyl or alkynyl of up to 4 carbon atoms, preferably methyl, ethyl, vinyl or ethynyl.

Reduction of the 17-keto group of a 4-androstene-3,17-dione derivative of Formula I is done by methods well known to a person skilled in the art. See, for example, John Fried: Organic Reactions in Steroid Chemistry, van Nostrand Reinhold Co., New York, etc. (1972) 1 : 61 et seq. These compounds can be reacted, for example, after ketalization, with sodium borohydride or lithium aluminum hydride to produce, after splitting of the ketal, a corresponding 17$\beta$-hydroxy-4-androsten-3-one of Formula III which are known to possess anabolic and/or androgenic activity.

Methods of alkylating a 17-keto group are likewise known. See, for example, John Fried: Organic Reactions in Steroid Chemistry, van Nostran Reinhold Col, New York, etc. (1972) 2 : 53 et seq. Thus, a 4-androstene-3,17-dione derivative of Formula I can be reacted, for example, optionally after ketalization of the 3-oxo group, with an alkyl magnesium halide, vinyllithium or an alkali metal acetylide, thus obtaining, after splitting the ketal group which may be present, a 17$\alpha$R-17$\beta$-hydroxy-4-androsten-3-one derivative of Formula III, which are known as pharmacologically active substances or intermediates for the preparation of other pharmacologically effective steroids.

The sterol derivatives of Formula II utilized as the starting compounds can be produced from the corresponding sterols by methods conventionally employed for the introduction of substituents at the 6- and/or 7-positions of steroids. References to such conversions are given in Carl Djerassi: Steroid Reactions; Holden Day Inc., San Francisco 1963 and John Fried and John A. Edwards: Organic Reactions in Steroid Chemistry; van Nostrand Reinhold Comp., New York 1972.

The following examples serve to explain the invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

A. Examples Concerning The Microbiological Side Chain Degradation

EXAMPLE 1

A 750 ml. Erlenmeyer flask is charged with 200 ml. of a sterile nutrient solution, containing 1% yeast extract, 0.45% of disodium hydrogen phosphate, 0.34% potassium dihydrogen phosphate, and 0.2% "Tween" 80, adjusted to pH 6.7. This is inoculated with a supernatant broth of a Mycobacterium spec. NRRL-B-3805 culture, and shaken for 3 days at 30° C. at 190 r.p.m.

A 50 l. fermentor with 40 l. of sterile nutrient solution, containing 1.23% yeast extract, 0.68% potassium dihydrogen phosphate, and 0.2% "Tween" 80, adjusted to pH 6.0, is inoculated with 200 ml. of the Mycobacterium spec. growth culture and incubated for 48 hours with aeration (2 m$^3$ per hour) at 30° C.

A 50 l. fermentor with 40 l. of nutrient solution, containing 2.0% corn steep liquor, 0.3% diammonium hydrogen phosphate, and 0.25% "Tween" 80, adjusted to pH 6.5, is combined, for induction, with 5 g. of 6 α-fluoro-4-cholesten-3-one and incubated for 24 hours with aeration (2 m$^3$ per hour) and agitation (200 r.p.m.) at 30° C.

Then, a solution of 20 g. of 6 α-fluoro-4-cholesten-3-one in 150 ml. of dimethylformamide, filtered under sterile conditions, is added to the culture, and the fermentation is continued for another 56 hours under agitation and aeration at 30° C.

After the fermentation has been completed, the culture is extracted three times with 5 l. portions of ethylene chloride; the extracts are concentrated under vacuum, and the residue is purified on a silica gel column, thus obtaining, after recrystallization from diisopropyl ether, 8.7 g. of 6 α-fluoro-4-androstene-3,17-dione, m.p. 229°–231° C.

Preparation of the Starting Material (a) 60 g. of 3β-hydroxy-5-cholestene is combined, in 360 ml. of absolute tetrahydrofuran and 120 ml. of methylene chloride, under ice cooling with 60 g. of N-bromosuccinimide. Thereafter, 120 ml. of pyridine:-hydrogen fluoride reagent (70% strength) is added thereto in incremental portions. The mixture is stirred for 1 hour with cooling and then stirred into ice water/-potassium carbonate. After ether extraction, the thus-obtained crude product is chromatographed on silica gel and recrystallized from methanol. The yield is 40.8 g. of 5-bromo-6β-fluoro-5α-cholestan-3β-ol, m.p. 114.5°–116° C.

(b) 30 g. of 5-bromo-6β-fluoro-5α-cholestan-3β-ol is dissolved in 730 ml. of acetone and combined, at 10° C., with 24.1 ml. of chromosulfuric acid, prepared from 267 g. of chromium (VI) oxide, 400 ml. of water, 230 ml. of concentrated sulfuric acid, filled up to a volume of 1000 ml. with water, The mixture is afitated for another 15 minutes at 10° C. and stirred into ice water. The precipitate is filtered off and taken up in methylene chloride. After drying and evaporation, the thus obtained crude product is dissolved in 290 ml. of acetic acid and agitated for 3 hours at 30° C. Then 4.65 g. of sodium acetate is added thereto and the mixture agitated for another 15 minutes at −30° C. The mixture is then precipitated into ice water, and the precipitate is filtered off and taken up in methylene chloride. The residue obtained after evaporation is chromatographed on silica gel and recrystallized from methanol, thus obtaining 14.5 g. of 6α-fluoro-4-cholesten-3-one, m.p. 111°–115° C.

In the same way, 5-stigmasten-3β-ol can be converted into the 6α-fluoro-4-stigmasten-3-one.

EXAMPLE 2

20 g. of 6α-fluoro-4-stigmasten-3-one (91.5% strength crude product) is reacted, under the conditions described in Example 1, with a Mycobacterium spec. NRRL-B-3805 culture thus obtaining 6.1 g. of 6α-fluoro-4-androstene-3,17-dione, m.p. 228°–231° C.

EXAMPLE 3

20 g. of 6α-fluoro-4-cholesten-3-one is reacted under the conditions of Example 1, but with the use of a culture of Mycobacterium phlei ATCC 354 and then worked up, thus obtaining 4.8 g. of 6α-fluoro-4-androstene-3,17-dione, m.p. 228°–231° C.

EXAMPLE 4

A 2 l. Erlenmeyer flask with 500 ml. of a sterile nutrient medium, containing 1% yeast extract, 0.45% disodium hydrogen phosphate, 0.34% potassium dihydrogen phosphate, and 0.2% "Tween" 80, adjusted to pH 6.7, is inoculated with a suspension of a Mycobacterium spec. NRRL-B-3805 dry culture and shaken for 3 days at 30° C. with 190 r.p. m.

Twenty Erlenmeyer flasks, each containing 100 ml. of a sterile nutrient medium with 2.0% corn steep liquor, 0.3% diammonium hydrogen phosphate, and 0.25% "Tween" 80, adjusted to pH 6.5, are each inoculated with 5 ml. of the Mycobacterium spec. growth culture and shaken for 24 hours at 30° C. and stirred at 220 r.p.m. Then, each culture is combined with 100 mg. of 7α-methyl-4-cholesten-3-one dissolved in 5 ml. of dimethylformamide, and the fermentation is continued for another 96 hours.

The combined cultures are extracted with ethylene chloride; the extract is concentrated under vacuum, and the residue is purified by chromatography over a silica gel column, thus obtaining after recrystallization from diisopropyl ether 0.8 g. of 7α-methyl-4-androstene-3,17-dione, m.p. 193°–194° C.

Preparation of the Starting Material 30 g. of cholesterol, 34.29 g. of lithium bromide, and 34.3 g. of lithium carbonate are suspended in 525 ml. of dimethyl-formamide, then heated to 75°–80° C. (internal temperature), and mixed dropwise within 45 minutes with 7.95 ml. of bromine in 170 ml. of dioxane. The mixture is further stirred for 2 hours, then 3 l. of water is stirred into the mixture. The latter is agitated for another 30 minutes, and then acidified under ice cooling with glacial acetic acid to pH 4 and extracted with ethyl acetate. The extracts are washed neutral with semisaturated NaCl solution, dried with sodium sulfate, and the solvent distilled off under vacuum.

Yield: 34.4 g. of a crude product which is purified by chromatography on silica gel. The subsequent crystallization from methanol produces 25.6 g. of 4,6-cholestadien-3-one, m.p. 80°–82.5° C.

From 7 g. of magnesium filings, 275 ml. of ether, and 6.26 ml. of methyl iodide, an ethereal methylmagnesium iodide solution is prepared in the usual way.

After the reaction, 550 ml. of absolute tetrahydrofuran is added dropwise to the reaction mixture, while removing the ether by distillation at the same time, until the internal temperature is 58°–60° C. Under intense ice cooling, 1.4 g. of copper(I) chloride is added thereto. After another 15 minutes, a solution of 27.5 g. of 4,6-cholestadien-3-one is added dropwise within 30 minutes to the reaction mixture. The latter is stirred for 2 hours, gently combined with 300 ml. of saturated ammonium chloride solution, diluted with 2 l. of ether, and worked up as usual. The crude product (28.7 g.) is dissolved in 250 ml. of tetrahydrofuran and, after the addition of 10 ml. of 2N sulfuric acid, heated under reflux for 2 hours. The usual working-up operation yields 26.3 g. of a crude product which is chromatographed on silica gel for purposes of purification, thus obtaining 16.6 g. of 7α-methyl-4-cholesten-3-one, m.p. 72/73°–75° C. (pentane).

EXAMPLE 5

Following the conditions of Example 4, 100 mg. portions of 6α-methyl-4-cholesten-3-one in twenty Erlenmeyer flasks with a Mycobacterium spec. NRRL-B-3805 culture and then worked up.

Yield: 0.8 g. of 6α-methyl-4-androstene-3,17-dione, m.p. 171°–174° C.

Preparation of the Starting Material 30 g. of cholesterol is dissolved in 600 ml. of methylene chloride and, under ice water cooling, 17.4 g. of m-chloroperbenzoic acid is added thereto in incremental portions over the course of 20 minutes. Thirty minutes after the last addition, the mixture is diluted with 200 ml. of methylene chloride and then extracted twice with 200 ml. portions of saturated sodium sulfate solution, twice with 200 ml. portions of diluted sodium bicarbonate solution, and thereafter with water until neutrality is attained. After drying over sodium sulfate, the solvent is distilled off under vacuum. The crude product is recrystallized from methanol, thus obtaining 23.4 g. of 3β-hydroxy-5,6-epoxycholesterol, m.p. 133°–136° C.

A methylmagnesium iodide solution is prepared from 3.64 g. of magnesium filings and 9.5 ml. of methyl iodide in 100 ml. of ether. Then, 20 g. of 3β-hydroxy-5,6-epoxy-cholesterol in 400 ml. of absolute toluene is added dropwise thereto, and the mixture is stirred for 45 hours at 60°–65° C. Under ice cooling, the mixture is then gently combined with 100 ml. of saturated ammonium chloride solution and worked up as usual. The crude product (21.3 g. of a brown, viscous oil) is dissolved in 400 ml. of benzene and refluxed for 21 hours after added 100 ml. of cyclohexanone and 20 g. of aluminum isopropylate. The cooled solution is diluted with benzene, extracted repeatedly with 1N sulfuric acid, and washed neutral with water.

The crude product is chromatographed on silica gel for purification. After crystallization from methanol, the yield is 12.75 g. of 6α-methyl-4-cholesten-3-one, m.p. 151–154° C.

B. Examples Concerning the Chemical Further Processing of the 4-Androstene-3,17-dione Derivatives

EXAMPLE 1

3.2 g. of 6α-fluoro-4-androstene-3,17-dione is dissolved in 50 ml. of isopropanol, cooled to 0° C., and combined with 135 mg. of finely pulverized sodium borohydride. The mixture is agitated for 3 hours at 0° C., acidified to pH 5 with 1N sulfuric acid, and concentrated exhaustively under vacuum. The residue is extracted with methylene chloride, the extract is washed, concentrated under vacuum, and recrystallized from diisopropyl ether, thus obtaining 2.05 g. of 6α-fluoro-4-androsten-17β-ol, m.p. 156°–158° C., which, as is known, is a strongly anabolic compound. (Steroids 3 (1964) : 109.

EXAMPLE 2

4.6 g. of 7α-methyl-4-androstene-3,17-dione is suspended in 20 ml. of methanol and 5 ml. of the trimethyl ester of orthoformic acid. After adding 50 mg. of p-toluenesulfonic acid, the mixture is heated to boiling for 2 hours. After cooling to 15° C., 4 ml. of acetone is added. The mixture is stirred for 90 minutes at 15° C., and then 0.1 ml. of triethylamine is introduced.

The precipitate is filtered off, washed with a small amount of methanol, and dried under vacuum at 20° C. The crude product is dissolved in 40 ml. of absolute ether and added dropwise within 10 minutes at room temperature to a methyllithium solution prepared from 1.5 g. of lithium and 9 ml. of methyl iodide in 100 ml. of ether. The mixture is then refluxed for 16 hours, cooled to 0° C., and 50 ml. of 2N sulfuric acid is carefully added thereto. The mixture is then heated for 2 hours under reflux and intense agitation. The usual working-up operation yields 3.71 g. of 17β-hydroxy-7α,17α-dimethyl-4-androsten-3-one, m.p. 163°–165° C. (from diisopropyl ether) which, as is known, is a strongly anabolic compound. J. Amer. Chem. Soc. 81 (1959) : 4069.

EXAMPLE 3

Under agitation, acetylene is passed for one hour into a mixture, cooled to 10° C., of 3.5 g. of potassium tert.-butylate in 65 ml. of absolute tetrahydrofuran. Then, 5.86 g. of 6α-methyl-4-androstene-3,17-dione is added thereto, and acetylene is introduced for another 90 minutes. The reaction mixture is thereafter combined with 50 ml. of methanol and 3 ml. of 4N hydrochloric acid, heated for one hour under reflux, and exhaustively concentrated under vacuum. The mixture is worked up as usual, thus obtaining 4.61 g. of 17α-ethynyl-17β-hydroxy-6α-methyl-4-androsten-3-one, m.p. 194°–196° C. (from methanol-tetrahydrofuran), which, as is known, is a compound having a strong progestational activity, J. Amer. Chem. Soc. 80 (1958) : 4717.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a 4-androstene-3,17-dione of the formula

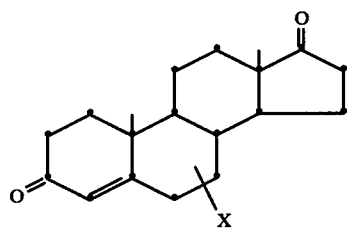

wherein X is 6,7-methylene or 6- or 7-fluoro, chloro, or methyl, comprising fermenting, in the absence of inhibitors, a sterol of the formula

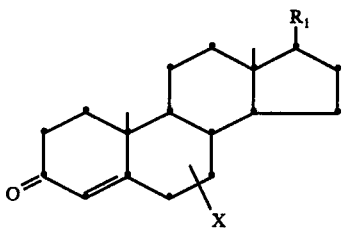

wherein X is as above and $R_1$ is a saturated or unsaturated sterol side chain of 8–10 carbon atoms, with a microorganism culture capable of degrading sterol side chains.

2. The process of claim 1, comprising the further step of either (a) selectively reducing the 17-keto group of the thus-produced 4-androstene-3,17-dione; or (b) selectively reacting the 17-keto group of the thus-produced 4-androstene-3,17-dione with an organometallic compound of the formula $$MeR_4$$

wherein $R_4$ is alkyl, alkenyl or alkynyl of up to 4 carbon atoms and Me is an alkali metal atom or a magnesium halide radical, to produce a 17β-hydroxy-4-androsten-3-one of the formula

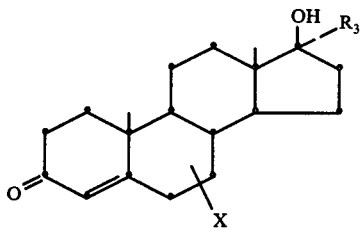

wherein X is 6,7-methylene or 6- or 7-fluoro, chloro, or methyl and $R_3$ is hydrogen or $R_4$, respectively.

3. The process of claim 2, comprising the additional steps of ketalizing the carbonyl at the 3-position of the 4-androstene-3,17-dione compound prior to the selective reduction or selective reaction, and subsequently cleaving the ketal at the 3-position of the 17β-hydroxy-4-androstene-3-one compound after the selective reduction or selective reaction.

4. The process of claim 2, wherein $R_3$ is hydrogen, methyl, ethyl, vinyl or ethinyl.

5. The process of claim 1, wherein the microorganism culture is of the genera Arthrobacter, Brevibacterium, Microbacterium, Protaminobacter, Bacillus, Norcardia or Streptomyces.

6. The process of claim 1, wherein the microorganism culture of the genus Mycobacterium.

7. The process of claim 1, wherein the microorganism culture is Mycobacterium spec. NRRL-B-3805 or *Mycobacterium phlei* ATCC 354.

8. The process of claim 2, wherein the microorganism culture is of the genera Arthrobacter, Brevibacterium, Microbacterium, Protaminobacter, Bacillus, Norcardia or Streptomyces.

9. The process of claim 2, wherein the microorganism culture of the genus Mycobacterium.

10. The process of claim 2, wherein the microorganism culture is Mycobacterium spec. NRRL-B-3805 or *Mycobacterium phlei* ATCC 354.

* * * * *